US008622377B2

(12) United States Patent
Konrad et al.

(10) Patent No.: US 8,622,377 B2
(45) Date of Patent: Jan. 7, 2014

(54) HOLDER FOR CAD/CAM BLANKS

(75) Inventors: Erich Konrad, Feldkirch-Nofels (AT);
Walter Entner, Rankweil (AT)

(73) Assignee: Ivoclar Vivadent AG, Schaan (LI)

( * ) Notice: Subject to any disclaimer, the term of this patent is extended or adjusted under 35 U.S.C. 154(b) by 1173 days.

(21) Appl. No.: 12/544,340

(22) Filed: Aug. 20, 2009

(65) Prior Publication Data

US 2011/0042880 A1 Feb. 24, 2011

(51) Int. Cl.
*B23Q 3/00* (2006.01)

(52) U.S. Cl.
USPC .......................................... 269/287; 269/309

(58) Field of Classification Search
CPC ...................................................... B25B 11/00
USPC ......... 269/287, 297, 303, 309–310, 313–314, 269/900; 279/77, 51, 2.06; 433/202.1, 173, 433/212.1; 81/177.85, 177.5, 53.2
See application file for complete search history.

(56) References Cited

U.S. PATENT DOCUMENTS

| | | | | |
|---|---|---|---|---|
| 2,912,890 | A | * | 11/1959 | Robinson ........................ 81/53.2 |
| 5,257,557 | A | * | 11/1993 | Battten ........................ 81/177.85 |
| 6,131,261 | A | * | 10/2000 | Michlin ............................ 29/251 |
| 6,224,371 | B1 | | 5/2001 | DeLuca |
| 6,482,284 | B1 | | 11/2002 | Reidt et al. |
| 6,485,305 | B1 | | 11/2002 | Pfeiffer |
| 6,627,327 | B2 | | 9/2003 | Reidt et al. |
| 6,660,400 | B1 | | 12/2003 | Hintersehr |
| 6,669,875 | B2 | | 12/2003 | Meyertholen et al. |
| 6,769,912 | B2 | | 8/2004 | Beuschel et al. |
| 6,878,456 | B2 | * | 4/2005 | Castro et al. ................ 428/542.8 |
| 6,979,496 | B2 | | 12/2005 | Haymann et al. |
| 6,991,853 | B2 | | 1/2006 | Branco de Luca et al. |
| 7,007,574 | B1 | * | 3/2006 | Wu .............................. 81/177.85 |
| 7,214,435 | B2 | | 5/2007 | Meyertholen et al. |
| 8,006,361 | B2 | * | 8/2011 | Hutter et al. .............. 29/243.518 |
| 2001/0036617 | A1 | * | 11/2001 | Karmaker et al. ............. 433/173 |
| 2002/0086266 | A1 | * | 7/2002 | Karmaker et al. .......... 433/202.1 |
| 2003/0031984 | A1 | * | 2/2003 | Rusin et al. .................... 433/215 |
| 2003/0168795 | A1 | * | 9/2003 | Fries .............................. 269/309 |
| 2004/0106087 | A1 | * | 6/2004 | Weigl et al. ................... 433/218 |
| 2007/0063456 | A1 | * | 3/2007 | Troxler ......................... 279/156 |
| 2009/0075238 | A1 | | 3/2009 | Galehr |
| 2010/0028834 | A1 | | 2/2010 | Galehr |
| 2011/0042880 | A1 | * | 2/2011 | Konrad et al. ................ 269/287 |
| 2011/0215538 | A1 | * | 9/2011 | Cornwell et al. ............... 279/82 |
| 2012/0074659 | A1 | * | 3/2012 | Fanourgiakis et al. ....... 279/145 |

FOREIGN PATENT DOCUMENTS

DE 102004020192 A1 10/2005

* cited by examiner

*Primary Examiner* — Lee D Wilson
(74) *Attorney, Agent, or Firm* — Ann M. Knab; Thad McMurray

(57) ABSTRACT

A holder for affixing a mill blank for the manufacture of a dental article in a housing of a milling unit of a CAD/CAM system, wherein the holder includes a joining surface for joining to the mill blank, a securing shaft having at least one securing surface for securing to a housing of a milling unit of a CAD/CAM system, wherein the securing shaft comprises an essentially polygonal shape with at least two lateral surfaces, wherein at least two of the lateral surfaces are arranged adjacent to each other and extend at right angles to each other; and wherein the securing surface, in cross-sectional view, extends substantially perpendicular to a radius of the securing shaft extending essentially through the center of the securing surface and comprises a width that is less than the width of a lateral surface.

35 Claims, 3 Drawing Sheets

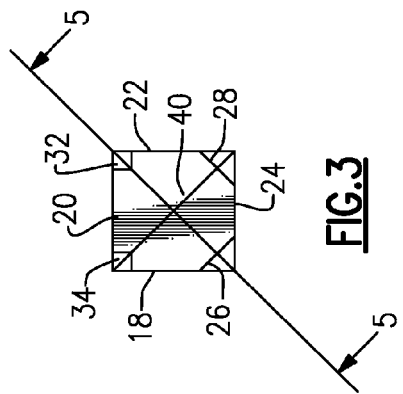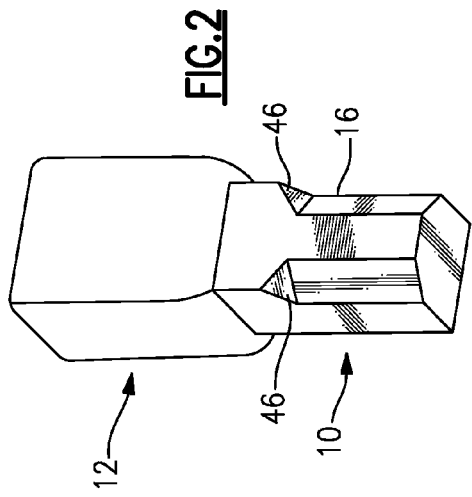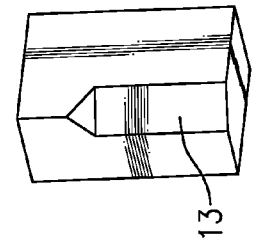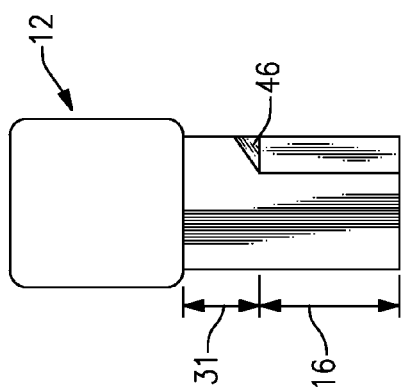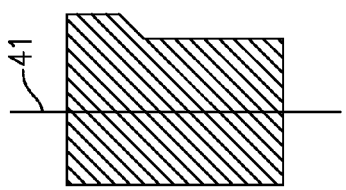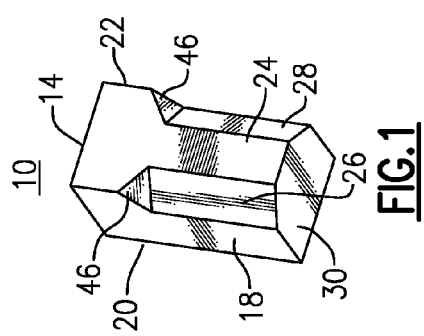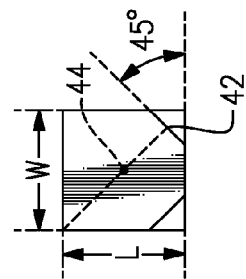

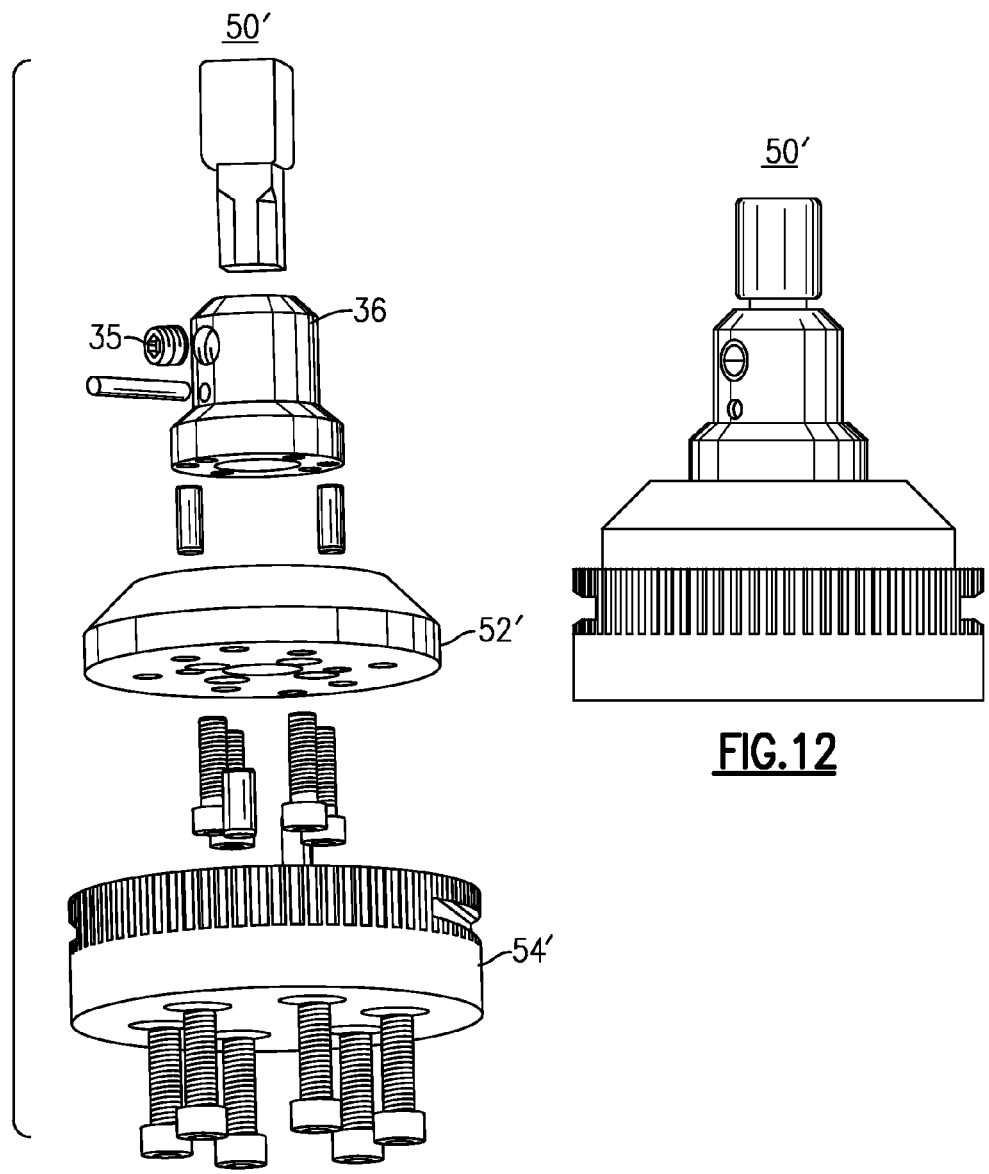
FIG. 10
FIG. 12
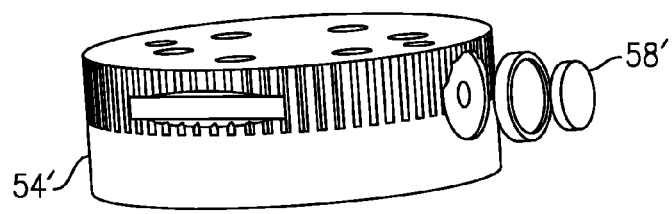
FIG. 11

HOLDER FOR CAD/CAM BLANKS

FIELD OF THE INVENTION

Embodiments of the present invention are directed to holders for CAD/CAM blanks for use in CAD/CAM systems, and more particularly to holders used in dental CAD/CAM systems.

BACKGROUND OF THE INVENTION

In the discussion that follows, reference is made to certain structures and/or methods. However, the following references should not be construed as an admission that these structures and/or methods constitute prior art. Applicant expressly reserves the right to demonstrate that such structures and/or methods do not qualify as prior art.

Today, there is a progressively increasing trend in dentistry toward the use of automated technologies for treatment planning, virtual procedures, orthodontics, design and manufacturing of dental restorations both in dental offices (chair side) and dental laboratories (lab side). This trend, sometimes called "digital revolution," is most evident in lab side explosion of CAD/CAM technologies. A number of CAD/CAM systems available to dental laboratories has increased nearly ten-fold in the last decade. Currently, there are over 25 dental CAD/CAM systems and quite a few copy-milling systems using mill blanks in a variety of shapes and sizes. Blank shapes vary from simple geometries such as rectangular, cylindrical or hexagonal to more complex such as smart blanks described in U.S. Pat. No. 6,979,496 which is incorporated by reference herein in its entirety. Their sizes range from about 0.5" to about 4" in length or diameter. Mill blanks are available in all 4 types of materials—metals, polymers (resins, plastics), ceramics and composites. Ceramic mill blanks can be divided into three major categories: feldspathic (leucite-based and sanidine or feldspar-based), glass-ceramic (lithium silicate, micaceous, etc.), and crystalline ceramic based such as alumina and/or zirconia (soft-sintered or fully dense). All three ceramic categories as well as composite blanks are already available or soon will be available in a variety of shades. Stocking the necessary inventory of shades for each given type of blank adds to economic pressures on the facility operating a CAD/CAM system.

While CAD/CAM technology provides dental laboratories with opportunities for improved quality, reproducibility and elimination of human error, most CAD/CAM systems are geared to milling soft-sintered zirconia and thus lacking material selection to be competitive in a supersaturated and fast-paced market. Since the price for a CAD/CAM system, depending on manufacturer and configuration, runs from $50,000 to $500,000 only the largest labs and outsource centers can afford to operate multiple systems to expand their material selection. Most CAD/CAM systems manufacturers do not make their own blocks, rather they purchase them from suppliers such as Ivoclar, Vita or Metoxit, with an established core competency in dental or advanced materials development and manufacturing. Understandably, CAD/CAM materials are fairly expensive adding substantially to CAD/CAM system operating costs. For example, the price of ceramic milling blanks range from about $0.60 to $4.50 per gram of material. Yield per blank as defined in U.S. Pat. No. 6,979,496 is fairly low and most of it goes to waste.

The first CAD/CAM systems comprising milling units for chair side or lab side use such as Cerec (Sirona) and Lava (3M/ESPE) were closed systems wherein mill blanks are attached to a stub retainer, projection, mandrel, holder or carrier body, which have a unique patented geometry as described in U.S. Pat. Nos. 6,485,305 and 6,769,912 and can be also protected by a bar-code, thereby preventing interchangeability with other (CAD/CAM) systems. Variations of a work piece (millable part) on a stub assembly are also described in U.S. Pat. Nos. 7,214,435, 6,669,875, 6,627,327, 6,482,284, 6,224,371, 6,991,853 and 6,660,400, which are hereby incorporated by reference. With advent of the open architecture systems, blank interchangeability between systems has become not only possible but extremely desirable. While the market is currently dominated by closed systems, the market penetration of open systems is steadily increasing. From 25 commercial CAD/CAM systems at least 5 or 6 are utilizing the same D-250 dental 3D scanner and DentalDesigner™ dental CAD software (3Shape A/S, Copenhagen, Denmark). In an open architecture system, the blanks are not bar-code protected and any blank can be used as long as it fits the existing housing (blank holder, chuck, collect, support) of the milling unit.

Thus, a need exists in the art for enabling blank and holder interchangeability, maximizing yield per blank, and reducing material waste, to maximize the system's versatility, selection of materials and efficiency of operation.

SUMMARY OF THE INVENTION

While the present invention is described herein mainly with reference to machining dental prostheses, it should be understood that the present invention is not so limited. For example, the principles of the present invention can be applied to medical devices in general (e.g., implants, replacement joint parts, skeletal replacements, etc.) According to its broader aspects, the present invention can apply to the milling or shaping of essentially any three-dimensional object.

It is a primary object of an embodiment of the present invention to provide a holder for affixing a mill blank for the manufacture of a dental article in a housing of a milling unit of a CAD/CAM system, wherein the holder includes a joining surface for joining to the mill blank, a securing shaft connected to the joining surface at its upper end, the securing shaft having a series of lateral surfaces and a bottom surface. The securing shaft includes at least one securing surface for securing to a housing of a milling unit of a CAD/CAM system, wherein the securing surface, in cross-sectional view, extends substantially perpendicular to a radius of the securing shaft extending essentially through the center of the securing surface and comprises a width that is less than the width of a lateral surface. The securing shaft, in cross-sectional view, comprises an essentially polygonal shape with at least two lateral surfaces, wherein at least two of the lateral surfaces are arranged adjacent to each other and extend at right angles to each other. The extension of the radius, which extends through the center of the securing surface, extends through the corner of one of the right angles. The securing surface may exhibit a width in the range of from about 0.3 to about 0.6 the length of a lateral surface. The width of the securing surface may be less than about 0.5 the width of a lateral surface. Moreover, the width of the securing surface may be about ($\sqrt{2}-1$) (approximately 0.4142) the width of a lateral surface not adjacent to the securing surface. Alternatively, the width of the securing surface may be approximately the same width of a lateral surface positioned between two securing surfaces.

According to another aspect of the holder, in cross-sectional view, the securing shaft has a ratio of length to width of approximately 1:1. A transition between adjacent lateral surfaces is formed by the at least one securing surface which extends transversely to both adjacent lateral surfaces at an angle of approximately 45 degrees. The minimum distance between the securing surface and the axis of the securing shaft may be approximately the same as the minimum distance between a lateral surface and the axis of the securing shaft.

According to a further aspect of the holder, the width of the securing surface is approximately one-third the width of a lateral surface. A line perpendicular to the middle of the width of the securing surface passes through the axis of the securing shaft.

According to yet another aspect of the holder, the securing surface extends parallel to the holder axis and is smaller than at least one lateral surface when viewed in the peripheral direction. The securing surface comprises a bevel extending substantially at an angle of 135 degrees from the at least one securing surface, although the position of the bevel is not limited to this angle and it may be positioned at any angle that provides ease of movement of the holder in a housing of a milling unit of a CAD/CAM system. The securing shaft may exhibit a height that is less than the height of the holder and the securing surface may exhibit a height of more than one-half the height of the holder.

According to a further aspect of the holder, the joining surface may be square-shaped and is passed through by the holder axis. The joining surface may include a flange or platform located at an end of the securing shaft, the flange or platform projecting radially over the securing shaft.

According to yet another aspect of the holder, the height of the holder is greater than the distance between opposing lateral surfaces. The holder includes a bottom surface opposing the joining surface, the bottom surface extending substantially parallel to the joining surface for positioning onto a housing of a milling unit of a CAD/CAM system.

According to a further aspect of the holder, the at least one securing surface comprises a first and a second securing surface, the first securing surface and the second securing surface each comprising a bevel, wherein the lateral surfaces of the securing shaft, when viewed in cross-section, are largest in width when the bevels of the first and second securing surfaces are disposed one after the other in the securing shaft.

According to yet another aspect of the holder, the mill blank attachable to the holder is rectangular in cross-section and projects over the cross-section of the securing shaft on all sides. The height of the milling blank, viewed from the axial direction, substantially corresponds to the total height of the securing shaft. The mill blank may be mechanically fastened, adhesively secured, or integrally attached to the holder. The mill blank may be fabricated of ceramic, polymer, composite, metal, or a combination thereof.

According to still a further aspect, the holder is directly attachable to the housing of a milling unit of a CAD/CAM system or attachable to at least one intermediate piece that is attachable to the housing of a milling unit of a CAD/CAM system. The holder is preferably secured to clamping hardware, the clamping hardware directly attachable to the housing of a milling unit or to an adapter attachable to the housing of a milling unit of a CAD/CAM system.

According to another aspect of the holder, the at least one securing surface is configured for securing to the clamping hardware by a mechanical component, by interference fit or by snap fit. The mechanical component may have a diameter that substantially corresponds to the diameter of the at least one securing surface. Optionally, the at least one securing surface may include at least one notch or undercut configured for form-fit connection with the clamping hardware.

According to a further aspect, the holder may be used in any type of CAD/CAM system including, but not limited to, 5-axis or 6-axis milling machines. The holder may be fabricated of a metal, resin, ceramic material or a combination thereof. Examples of three-dimensional objects for manufacturing herein include, but are not limited to, dental articles, such as, a coping, pontic, framework, denture teeth, space maintainer, tooth replacement appliance, orthodontic retainer, denture, post, facet, splint, cylinder, pin, connector, crown, partial crown, veneer, onlay, inlay, bridge, fixed partial denture, implant or abutment.

BRIEF DESCRIPTION OF THE DRAWING FIGURES

FIG. 1 is a perspective view of a holder according to an embodiment of the present invention.

FIG. 2 is a perspective view of the holder of FIG. 1 having a mill blank attached thereto.

FIG. 3 is a bottom plan view of the holder of FIG. 1.

FIG. 4 is a bottom plan view of the holder of FIG. 1.

FIG. 5 is a sectional view of the holder of FIG. 1 taken at line 5-5 in FIG. 3.

FIG. 6 is a perspective side view of the holder and mill blank of FIG. 2.

FIG. 7 is a perspective view of a holder according to an embodiment of the present invention.

FIG. 10 is an exploded view of the components in another housing assembly of a CAD/CAM system with the holder of FIG. 1.

FIG. 11 is a perspective view of the pallet of the housing assembly of FIG. 10.

FIG. 12 is a perspective view of the assembled components of the housing assembly of FIG. 10.

DETAILED DESCRIPTION OF THE INVENTION

Figures 8, 9:
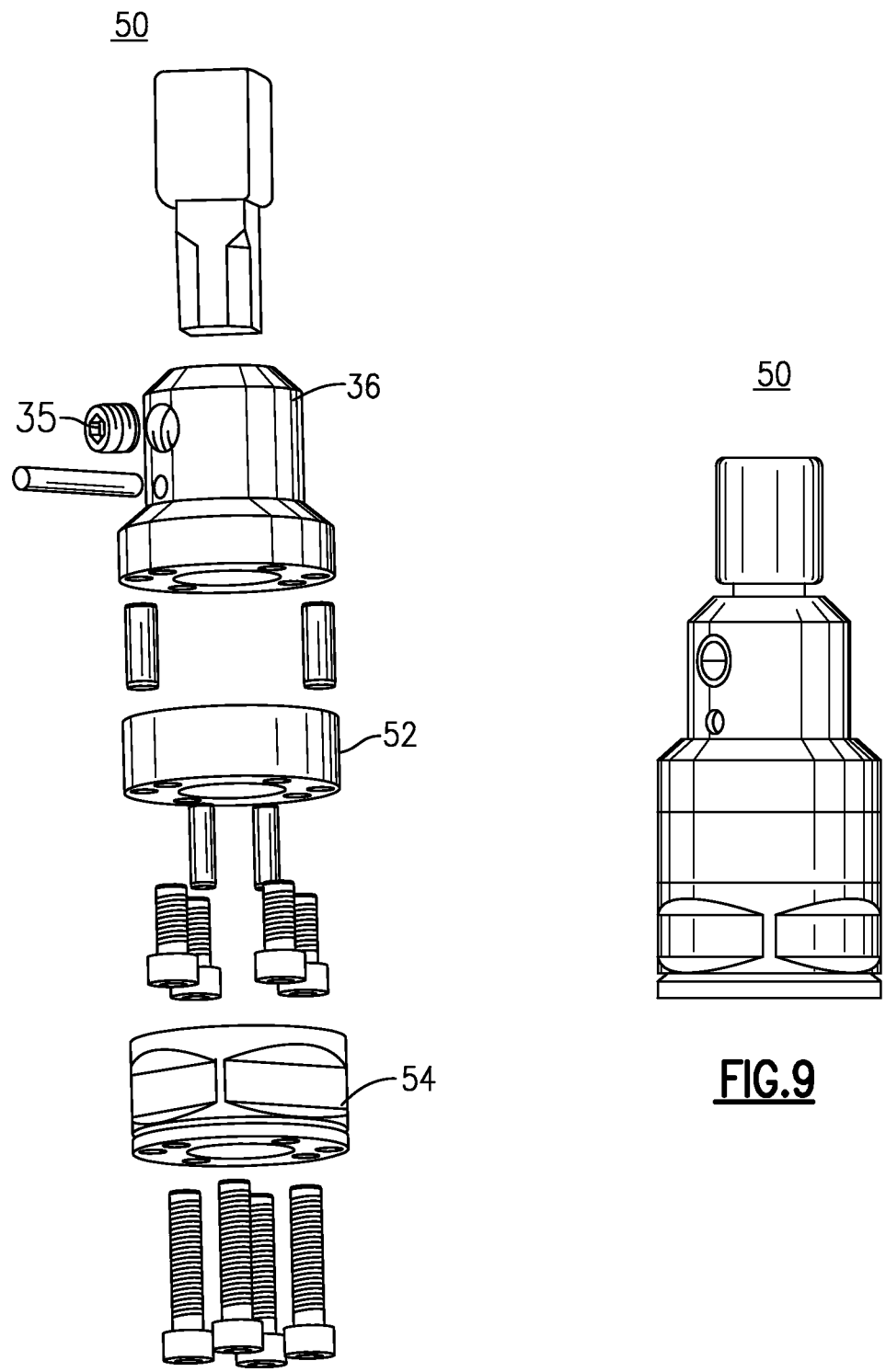
FIG. 8 is an exploded view of the components in a housing assembly of a CAD/CAM system with the holder of FIG. 1.
FIG. 9 is a perspective view of the assembled components of the housing assembly of FIG. 7.

"Present invention" means at least some embodiments of the present invention; references to various feature(s) of the "present invention" throughout this document do not mean that all claimed embodiments or methods include the referenced feature(s). It should be mentioned that any references, including patents, patent applications and published articles that are cited herein are incorporated by reference in their entirety. Any word used herein in plural form may also include singular forms of the word and any word used in singular form herein may also include plural forms of the word.

As will be appreciated, an embodiment of the present invention provides a holder 10 as shown in FIG. 1 for affixing a mill blank 12 as shown in FIG. 2 to a housing of a milling unit of a CAD/CAM system. Holder 10 is preferably a single, unitary component that comprises a connecting or joining surface 14 and a securing shaft 16. Joining surface 14 is preferably positioned at the upper end of securing shaft 16 of holder 10 for attaching mill blank 12 to holder 10. Mill blank 12 may be joined to holder 10 by mechanically fastening, adhesively securing, or integrally attaching to holder 10. Joining surface 14 is a preferably in the form of a platform or flange which extends over at least a portion of securing shaft 16.

Securing shaft 16 secures holder 10 to a housing of a milling unit (shown in FIGS. 8 and 10 and described below). Securing shaft 16 securely fastens holder 10 to the housing of a milling unit such that mill blank 12 is machined without vibration or play (uncontrolled movement as blank moves as well) of blank 12 or holder 10 in the milling unit of the CAD/CAM system. Holder 10 may be fabricated of ceramic, polymer, composite, metal, or a combination thereof.

Securing shaft 16 includes a series of longitudinally extending lateral surfaces or sides 18, 20, 22 and 24 and at least one securing surface 26. At least one securing surface is included in securing shaft 16 and as many securing surfaces as desired may be included in shaft 16. Shaft 16 includes a second securing surface 28. Securing surfaces 26 and 28 are the means used to actually secure holder 10 to the housing into which it is inserted. Only one surface 26 or 28 may be necessary to secure holder 10 to the housing. Reference is made to FIG. 7, which shows an alternative embodiment of holder 11 having a single securing surface 13.

FIG. 3 is a cross-sectional view of holder 10 as viewed from the bottom surface 30. The angle of bottom surface 30 is not limited to a specific orientation, although it is preferable that bottom surface 30 is substantially parallel to joining surface 14. The orientation of bottom surface 30 may be depend on the shape and configuration of the housing into which holder 10 is positioned. The cross-section of holder 10, as viewed from bottom side 26 includes two right angles 32 and 34 formed by lateral surfaces 22 and 20, and lateral surfaces 18 and 20, respectively. Securing surfaces 26 and 28 are transition surfaces between lateral surfaces 18 and 24, and lateral surfaces 24 and 28, respectively angled to provide space for insertion and connection to a housing. The angle of the securing surfaces 26 and 28 allow for contact with clamping hardware when shaft 16 is inserted into a housing. Reference is made to FIGS. 8 and 10, which show a clamping element 35, such as a screw, that is screwed into a clamping chuck 36 to secure shaft 16 to clamping surface or chuck 36. Using a clamping element is but one example of securing holder 10 to clamping hardware. Other methods include, but are not limited to, fitting holder 10 into the housing by interference, such as snap-fit or press-fit.

Securing surfaces 26 and 28 extend substantially perpendicular to a radius of diameter 40 extending through the center of the securing surface 26 or 28, which extends through the axis of the securing shaft to a corner of a right angle 32 or 34, respectively. It is preferable that securing surfaces 26 and 28 extend substantially parallel to the axis 41 of the securing shaft 16, shown in FIG. 5. It is further preferable that the length and the width of shaft 16 is substantially similar, as viewed form the cross-sectional view in FIG. 4, i.e., the ratio between the length and width is approximately 1:1, although this is not a limitation of the width and length of shaft 16, which can be any length and width. The width of securing surfaces 26 and 28 is preferably less than the width of a lateral surface, and more preferably about one-third to about one-half the width of a lateral surface. When viewing the securing surfaces 26 and 28 from a peripheral direction, such as shown in FIGS. 1 and 2, is it preferred that the securing surfaces are smaller than at least one lateral surface, 18, 20, 22 or 24.

The angle at which the securing surfaces 26 and 28 make with adjacent lateral surfaces is approximately 45 degrees, as shown in FIG. 4, although the angle at which the securing surfaces make with lateral surfaces is not limited to a specific angle. It is preferable that the middle 42 of the width of the securing surfaces 26 and 28 passes through the axis 44 of the securing shaft 16.

Reference is made to FIGS. 1, 2 and 6, which show a bevel 46 proximate the top or upper surface of securing surfaces 26 and 28. Bevel 46 is shown positioned at an angle of 135 degrees with respect to securing surfaces 26, 28, although the angle of position of bevel 46 is not limited to a specific angle.

FIG. 5 is a cross-sectional view of holder 10 taken at line 5-5 in FIG. 3. The angle of the bevel with securing surface 26 is clearly seen.

Securing surfaces 26, 28 may be located on any point of shaft 16. It is preferable that they are disposed one after the other, as shown. Accordingly, lateral surfaces are of greatest width when securing surfaces are positioned adjacent, i.e., surface 20 has no disruption in length, in comparison to a design having securing surfaces 16, 28 disposed opposite or across from each other.

Securing shaft 16 may be shorter in length than holder 10 or may extend from bottom surface 30 to joining surface 14. Securing surface may extend any length on holder 10, preferably to a length that is more than one-half the length of holder 10. Although there is no limitation on the height of holder 10, it is preferably that the height is greater than the distance between opposing lateral surfaces. In an alternative embodiment, joining surface 14 may be in the form of a joining shaft 31 that extends from top joining surface 14 to the lower end of bevel 46 and securing shaft 16 may extend from the bottom of bevel 46 to the bottom surface 30.

Joining surface 14 may be any shape, including polygonal, circular, oval or oblong. Preferably, joining surface 14 is square-shaped to easily accommodate the cross-sectional rectangular or square shape of a mill blank. Mill blanks are not limited to rectangular and square shapes and may be provided in other polygonal, circular, oval or oblong shapes and/or complex near-net shapes. The mill blank may fit within the area of joining surface 14 or extend over one or more edges, as shown in FIG. 2. The mill blank may be similar or different in height with respect to holder 10. FIG. 6 shows mill blank 12 with a height similar to the height of holder 10. The mill blank may be fabricated of a metal, resin, ceramic material, or a combination thereof. Dental articles that may be milled from the mill blank include, but are not limited to, a coping, pontic, framework, denture teeth, space maintainer, tooth replacement appliance, orthodontic retainer, denture, post, facet, splint, cylinder, pin, connector, crown, partial crown, veneer, onlay, inlay, bridge, fixed partial denture, implant or abutment.

Reference is made to FIGS. 8 through 11, which show CAD/CAM housing assemblies 50 and 50', respectively. Like parts are named with the same reference numbers, whereas different parts for the same purpose are distinguished by an apostrophe symbol.

Holder 10 can be inserted into a housing of a milling unit directly, or may be inserted into intermediate parts, which are then inserted into a housing of a milling unit. Typically, holder 10 will be inserted into and secured to a clamping hardware such as clamping chuck 36. Examples of means of securing or fastening to clamping chuck 36 include, but are not limited to, mechanical clamping components such as a bolt, screw, or set screws. If a clamping component is used, it is preferable that the diameter of the clamping component have a diameter similar to the width of securing surfaces 26, 28. Holder 10 may also be secured to chuck 36 by interference or press fit. Securing surfaces 26, 28 may be further configured to press fit into chuck 36. Configurations include, but are not limited to a notch, an undercut or other surface, such as that shown in U.S. Publication 20090075238, which is hereby incorporated by reference, that is configured for snap, press or interference fit into chuck 36

Clamping chuck 36 may be inserted into a housing of a milling unit directly or may be attached to an adapter 52 or 52', which is then inserted into a housing or pallet 54 or 54' of a milling unit. FIGS. 9 and 12 showed the assembled housing configurations, 50, 50'.

Reference is made to FIG. 11, which shows pallet 54' having a transponder 58', such as a radio-frequency identification (RFID) tag for providing information about the mill block, such as type of material, shade, strength, and other factors useful about the material. A sensor on the milling machine reads the RFID tag to determine the material on pallet 54' prior to the milling operation. A database linked to the milling machine associates a specific CAM file to the block of material and the machine mills the block in accordance with the CAM file.

When a new block is added to the holder and pallet, the information regarding the properties of the block of material may be input by an operator by the use of a barcode type scanner. The RFID tag 58' is scanned and the control panel is programmed to erase the prior information associated with the previous block of material. The new material information is then entered into the control panel. A database stores the information about the block of material on pallet 54'. When a new case is ready to be milled, the CAM file associated with the block on pallet 54' is utilized to mill the block accordingly.

Securing shaft 16 provides a facile means to secure holder 10 into a housing of a milling unit of a CAD/CAM system. It is adaptable to fit into many different types of CAD/CAM systems with the use of an adapter or similar component.

Although the present invention has been described in connection with preferred embodiments thereof, it will be appreciated by those skilled in the art that additions, deletions, modifications, and substitutions not specifically described may be made without department from the spirit and scope of the invention as defined in the appended claims.

What is claimed is:

1. A holder for affixing a mill blank for the manufacture of a dental article in a housing of a milling unit of a CAD/CAM system comprising
   a joining surface for joining the holder to the mill blank;
   a securing shaft connected to the joining surface, the securing shaft having at least one securing surface for securing to a housing;
   wherein the securing shaft, in cross-sectional view, comprises an essentially polygonal shape with at least two lateral surfaces, wherein at least two of the lateral surfaces are arranged adjacent to each other and extend at right angles to each other;
   wherein the securing surface, in cross-sectional view, extends substantially perpendicular to a radius of the securing shaft extending essentially through the center of the securing surface and comprises a width that is less than the width of a lateral surface; and
   wherein a transition between adjacent lateral surfaces is formed by the at least one securing surface which extends transversely to both adjacent lateral surfaces at an angle of approximately 45 degrees.

2. The holder of claim 1 wherein an extension of the radius extends through the corner of one of the right angles.

3. The holder of claim 1 wherein the width of the securing surface is about 0.3 to about 0.6 the length of a lateral surface.

4. The holder of claim 1 wherein the width of the securing surface is less than about 0.5 the width of a lateral surface.

5. The holder of claim 1 wherein the width of the securing surface is about $\sqrt{2}-1$ the width of a lateral surface not adjacent to the securing surface.

6. The holder of claim 1 wherein the width of the securing surface is approximately the same width of a lateral surface positioned between two securing surfaces.

7. The holder of claim 1 wherein the securing shaft, in cross-sectional view, has a ratio of length to width is approximately 1:1.

8. The holder of claim 1 wherein the width of the at least one securing surface is approximately one-third the width of a lateral surface.

9. The holder of claim 1 wherein a line perpendicular to the middle of the width of the at least one securing surface passes through the axis of the securing shaft.

10. The holder of claim 1 wherein the at least one securing surface extends parallel to the holder axis and is smaller than at least one lateral surface when viewed in the peripheral direction.

11. The holder of claim 1 wherein the at least one securing surface comprises a bevel extending substantially at an angle of 135 degrees from the at least one securing surface.

12. The holder of claim 11 wherein the at least one securing surface comprises a first and a second securing surface, the first and the second securing surfaces each comprising a bevel, wherein the lateral surfaces of the securing shaft, when viewed in cross-section, are largest in width when the bevels of the first and second securing surfaces are disposed one after the other in the securing shaft.

13. The holder of claim 1 wherein the securing shaft is shorter in height than the height of the holder and wherein the securing surface has a height of more than one-half the height of the holder.

14. The holder of claim 1 wherein the joining surface is square-shaped and is passed through by the holder axis.

15. The holder of claim 1 wherein the joining surface comprises a flange or platform located at an end of the securing shaft, the flange or platform projecting radially over the securing shaft.

16. The holder of claim 1 wherein the axial height of the holder is larger than the distance between opposing lateral surfaces.

17. The holder of claim 1 wherein the holder comprises a bottom surface opposing the joining surface, the bottom surface extending substantially parallel to the joining surface for positioning on the housing.

18. The holder of claim 1 wherein a mill blank is positioned on the joining surface of the holder, the mill blank is rectangular in cross-section and projects over the cross-section of the securing shaft on all sides.

19. The holder of claim 1 wherein a mill blank is positioned on the joining surface of the holder, the mill blank the height of the mill blank, viewed from the axial direction, substantially corresponds to the total height of the securing shaft.

20. The holder of claim 1 wherein the holder is directly attachable to the housing or attachable to at least one intermediate piece that is attachable to the housing.

21. The holder of claim 20 wherein the holder is secured to clamping hardware, the clamping hardware directly attachable to the housing of a milling unit or to an adapter attachable to the housing.

22. The holder of claim 21 wherein the at least one securing surface is configured for securing to the clamping hardware by a mechanical component, by interference fit or by snap fit.

23. The holder of claim 22 wherein the mechanical component comprises a diameter that substantially corresponds to the diameter of the at least one securing surface.

24. The holder of claim 22 wherein the at least one securing surface comprises at least one notch or undercut configured for form-fit connection with the clamping hardware.

25. The holder of claim 1 wherein the mill blank is mechanically fastened to, adhesively secured to, or integrally attached to the holder.

26. The holder of claim 1 wherein the holder is positioned in a CAD/CAM system, and wherein the CAD/CAM system is a 5-axis or 6-axis milling machine.

27. The holder of claim 1 wherein the holder is fabricated of a metal, resin or ceramic material.

28. The holder of claim 1, wherein a mill blank is attached to the holder and wherein the mill blank is formed into a dental article and wherein the dental article comprises a coping, pontic, framework, denture teeth, space maintainer, tooth replacement appliance, orthodontic retainer, denture, post, facet, splint, cylinder, pin, connector, crown, partial crown, veneer, onlay, inlay, bridge, fixed partial denture, implant or abutment.

29. The holder of claim 1 wherein a mill blank is attached to the holder and wherein the mill blank is fabricated of ceramic, polymer, composite, metal, or combination thereof.

30. The holder of claim 1 wherein the housing comprises a transponder for automatically conveying information about the block.

31. The holder of claim 30 wherein the transponder comprises an RFID tag.

32. The holder of claim 30 wherein the holder is positioned in a CAD/CAM system, and wherein the block information is associated with a CAM file of the CAD/CAM system, wherein the CAM file provides milling specifications for the article to be milled in the milling unit of the CAD/CAM system.

33. A holder for affixing a mill blank for the manufacture of a dental article in a housing of a milling unit of a CAD/CAM system comprising
a joining surface for joining the holder to the mill blank;
a securing shaft connected to the joining surface, the securing shaft having at least one securing surface for securing to a housing;
wherein the securing shaft, in cross-sectional view, comprises an essentially polygonal shape with at least two lateral surfaces, wherein at least two of the lateral surfaces are arranged adjacent to each other and extend at right angles to each other;
wherein the securing surface, in cross-sectional view, extends substantially perpendicular to a radius of the securing shaft extending essentially through the center of the securing surface and comprises a width that is less than the width of a lateral surface; and
wherein the at least one securing surface comprises a bevel extending substantially at an angle of 135 degrees from the at least one securing surface.

34. A holder for affixing a mill blank for the manufacture of a dental article in a housing of a milling unit of a CAD/CAM system comprising
a joining surface for joining the holder to the mill blank;
a securing shaft connected to the joining surface, the securing shaft having at least one securing surface for securing to a housing;
wherein the securing shaft, in cross-sectional view, comprises an essentially polygonal shape with at least two lateral surfaces, wherein at least two of the lateral surfaces are arranged adjacent to each other and extend at right angles to each other;
wherein the securing surface, in cross-sectional view, extends substantially perpendicular to a radius of the securing shaft extending essentially through the center of the securing surface and comprises a width that is less than the width of a lateral surface; and
wherein the housing comprises a transponder for automatically conveying information about the block.

35. The holder of claim 34 wherein the transponder comprises an RFID tag.

\* \* \* \* \*